US012642956B2

(12) United States Patent　　　　　(10) Patent No.:　US 12,642,956 B2
Belleville et al.　　　　　　　　　　　　(45) Date of Patent:　　*Jun. 2, 2026

(54) MULTI-CHANNEL OPTICAL PRESSURE SENSOR

(71) Applicant: Abiomed, Inc., Danvers, MA (US)

(72) Inventors: Claude Belleville, Danvers, MA (US); Andrew Gentile, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 308 days.

This patent is subject to a terminal disclaimer.

(21) Appl. No.: 18/340,119

(22) Filed: Jun. 23, 2023

(65) Prior Publication Data

US 2024/0123216 A1　　Apr. 18, 2024

Related U.S. Application Data

(60) Provisional application No. 63/355,231, filed on Jun. 24, 2022.

(51) Int. Cl.
　*G01N 21/55*　　　(2014.01)
　*A61M 60/13*　　　(2021.01)
　*A61M 60/816*　　(2021.01)
(52) U.S. Cl.
　CPC ... A61M 60/816 (2021.01); *A61M 2205/3331* (2013.01); *A61M 2210/125* (2013.01)
(58) Field of Classification Search
　CPC .... A61M 2205/103; A61M 2205/3306; A61M 2205/3327; A61M 2205/3344;
　　　　　　　　　(Continued)

(56) References Cited

U.S. PATENT DOCUMENTS 4,321,831 A　　3/1982　Tomlinson et al.
4,691,709 A　　9/1987　Cohen
　　　　　　(Continued)

FOREIGN PATENT DOCUMENTS

EP　　　　0895075 A2　　2/1999
WO　　2011022008 A1　　2/2011

OTHER PUBLICATIONS

Invitation to Pay Additional Fees Form PCT/ISA/206 of the International Searching Authority for Application No. PCT/US2023/026044, dated Oct. 12, 2023.

(Continued)

*Primary Examiner* — Jon Eric C Morales
(74) *Attorney, Agent, or Firm* — Pierce Atwood LLP

(57)　　　　　ABSTRACT

A multi-channel optical pressure sensor is provided. The multi-channel optical pressure sensor includes at least one LED configured to generate light having a first spectrum and a second spectrum, a plurality of sensors including a first sensor coupled to the at least one LED via at least one first optical fiber and a second sensor coupled to the at least one LED via at least one second optical fiber, and a detector module coupled to first sensor and the second sensor. The detector module comprises at least one lens and an image sensor configured to sense light received from the at least one lens. The multi-channel optical pressure sensor further includes at least one hardware processor configured to determine based, at least in part, on the light sensed by the image sensor, a first pressure measured at the first sensor and a second pressure measured at the second sensor.

20 Claims, 10 Drawing Sheets

(58) Field of Classification Search
CPC .............. A61M 60/816; A61M 60/221; A61M
60/237; A61M 60/508
See application file for complete search history.

(56) References Cited

U.S. PATENT DOCUMENTS

| | | | |
|---|---|---|---|
| 7,835,598 B2 | 11/2010 | Lopushansky et al. | |
| 2011/0097031 A1 | 4/2011 | Carralero et al. | |
| 2012/0147381 A1* | 6/2012 | LeBlanc | E21B 47/135 |
| | | | 385/33 |
| 2024/0216670 A1* | 7/2024 | Gentile | A61M 60/508 |
| 2025/0143034 A1* | 5/2025 | Belleville | G01L 1/242 |

OTHER PUBLICATIONS

International Search Report and Written Opinion of the International Searching Authority for Application No. PCT/US2023/026044, dated Dec. 4, 2023.

* cited by examiner

Correlation varies inversely with bandwidth

MULTI-CHANNEL OPTICAL PRESSURE SENSOR

RELATED APPLICATIONS

This application claims the benefit under 35 U.S.C. § 119(e) of U.S. Provisional Patent Application No. 63/355,231, entitled "MULTI-CHANNEL OPTICAL PRESSURE SENSOR," filed Jun. 24, 2022, the entire contents of which is incorporated by reference herein.

FIELD OF INVENTION

The disclosure relates to a multi-channel optical pressure sensor.

BACKGROUND

Fluid pumps, such as blood pumps, are used in the medical field in a wide range of applications and purposes. An intravascular blood pump is a pump that can be advanced through a patient's vasculature, i.e., veins and/or arteries, to a position in the patient's heart or elsewhere within the patient's circulatory system. For example, an intravascular blood pump may be inserted via a catheter and positioned to span a heart valve. The intravascular blood pump is typically disposed at the end of the catheter. Once in position, the pump may be used to assist the heart and pump blood through the circulatory system and, therefore, temporarily reduce workload on the patient's heart, such as to enable the heart to recover after a heart attack. An exemplary intravascular blood pump is available from ABIOMED, Inc., Danvers, MA under the tradename Impella ° heart pump.

Such pumps can be positioned, for example, in a cardiac chamber, such as the left ventricle, to assist the heart. In this case, the blood pump may be inserted via a femoral artery by means of a hollow catheter and introduced up to and into the left ventricle of a patient's heart. From this position, the blood pump inlet draws in blood and the blood pump outlet expels the blood into the aorta. In this manner, the heart's function may be replaced or at least assisted by operation of the pump.

An intravascular blood pump is typically connected to a respective external heart pump controller that controls the heart pump, such as motor speed, and collects and displays operational data about the blood pump, such as heart signal level, battery temperature, blood flow rate and plumbing integrity. An exemplary heart pump controller is available from ABIOMED, Inc. under the trade name Automated Impella Controller®. The controller may raise alarms when operational data values fall beyond predetermined values or ranges, for example if a leak, suction, and/or pump malfunction is detected. The controller may include a video display screen upon which is displayed a graphical user interface configured to display the operational data and/or alarms.

SUMMARY

Described herein are systems and methods for a multi-channel optical pressure sensor. The multi-channel optical pressure sensor may be incorporated into a heart pump in some embodiments. When incorporated into a heart pump, the multi-channel optical pressure sensor may be used to sense a differential pressure, such as across the aortic valve, when the heart pump is positioned within the heart of the patient. The differential pressure measurement may be used, for instance, to calculate the blood flow rate through the heart pump during its operation.

In some embodiments, a multi-channel optical pressure sensor is provided. The multi-channel optical sensor comprising at least one light-emitting diode (LED), a plurality of sensors including a first sensor coupled to the at least one LED via at least one first optical fiber and a second sensor coupled to the at least one LED via at least one second optical fiber, a detector module coupled to first sensor and the second sensor, the detector module comprising at least one lens, and an image sensor configured to sense light received from the at least one lens, and at least one hardware processor configured to determine based, at least in part, on the light sensed by the image sensor, a first pressure measured at the first sensor and a second pressure measured at the second sensor.

In one aspect, the at least one LED comprises a first LED configured to generate first light having a first spectrum, and a second LED configured to generate second light having a second spectrum. In one aspect, the first spectrum has a peak wavelength in a range of 550-670 nm and the second spectrum has a peak wavelength in a range of 800-900 nm. In one aspect, the first spectrum has a peak wavelength in the range of 550-600 nm. In one aspect, the first spectrum has a peak wavelength that is $\frac{4}{5}$ of a peak wavelength of the second spectrum. In one aspect, the first LED and/or the second LED is smaller than 1 mm. In one aspect, the first LED and/or the second LED is a Phosphor converted LED. In one aspect, the at least one LED comprises a single LED having a broad spectrum.

In one aspect, the sensor further comprises a first optical element arranged between the at least one LED and the plurality of sensors. The first optical element is configured to receive the first light and the second light, and output third light and fourth light, each of the third light and fourth light having a third spectrum. In one aspect, the sensor further comprises a second optical element coupled to the first optical element, the first sensor, and the detector module, and a third optical element coupled to the first optical element, the second sensor, and the detector module. In one aspect, the second optical element is configured to provide first reflected light from the first sensor to the detector module, and the third optical element is configured to provide second reflected light from the second sensor to the detector module.

In one aspect, the at least one lens comprises a plano lens. In one aspect, the plano lens comprises a set of D-shaped lenses having curved edges facing each other. In one aspect, the at least one lens is configured to reduce spherical aberration in the light received from the first sensor and the second sensor. In one aspect, the at least one lens is configured to magnify a light signal incident on the at least one lens. In one aspect, a magnification factor of the at least one lens is at least 1.1 and less than 3. In one aspect, the magnification factor is at least 1.1 and less than 2. In one aspect, the magnification factor is less than 1.5. In one aspect, the magnification factor is less than 1.3. In one aspect, the at least one lens includes at least two lenses that collectively magnify the light signal incident on the at least one lens. In one aspect, the at least two lenses comprise a first lens having a first focal length and a second lens having a second focal length different from the first focal length. In one aspect, each of the first lens and the second lens is a D-shaped lens having a curved edge, and the curved edges of the first and second lenses are arranged to face each other.

In one aspect, the detector module further comprises a Fizeau arranged between the at least one lens and the image sensor. In one aspect, the image sensor comprises a two-dimensional image sensor. In one aspect, the at least one lens and the Fizeau are configured to collectively project the light received from the first and second sensors as two lines on the two-dimensional image sensor. In one aspect, the two lines are two parallel lines. In one aspect, each of the two lines on the two-dimensional image sensor comprises an interferogram, and wherein determining based, at least in part, on the light sensed by the image sensor, a first pressure measured at the first sensor and a second pressure measured at the second sensor comprises determining the first pressure and the second pressure based on a corresponding interferogram.

In some embodiments, a circulatory support device is provided. The circulatory support device comprises a rotor, a motor configured to drive rotation of the rotor at one or more speeds, a first optical pressure sensor configured to detect a first pressure signal, a second optical pressure sensor configured to detect a second pressure signal, and at least one hardware processor. The at least one hardware processor is configured to determine a differential pressure signal based, at least in part, on the first pressure signal and the second pressure signal.

In one aspect, the at least one hardware processor is further configured to determine a flow rate through the circulatory support device based, at least in part, on the differential pressure signal. In one aspect, the circulatory support device further comprises a first light emitting diode (LED) coupled to the first optical pressure sensor and the second optical pressure sensor, the first LED being configured to generate first light having a first spectrum, and a second LED coupled to the first optical pressure sensor and the second optical pressure sensor, the second LED being configured to generate second light having a second spectrum. In one aspect, the first spectrum has a peak wavelength in the range of 550-670 nm and the second spectrum has a peak wavelength in the range of 800-900 nm. In one aspect, the first spectrum has a peak wavelength in the range of 550-600 nm. In one aspect, the first spectrum has a peak wavelength that is 4/5 of a peak wavelength of the second spectrum. In one aspect, the first LED and/or the second LED is smaller than 1 mm. In one aspect, the first LED and/or the second LED is a Phosphor converted LED.

In one aspect, the circulatory support device further comprises a first optical element arranged to receive the first light and the second light, and output third light and fourth light, each of the third light having a third spectrum, the third light being provided to the first optical pressure sensor and the fourth light being provided to the second optical pressure sensor. In one aspect, the circulatory support device further comprises a second optical element coupled to the first optical element and the first optical pressure sensor, and a third optical element coupled to the first optical element and the second optical pressure sensor. In one aspect, the circulatory support device further comprises a detector module, wherein the second optical element is configured to provide first reflected light from the first optical pressure sensor to the detector module, and the third optical element is configured to provide second reflected light from the second optical pressure sensor to the detector module.

In one aspect, the circulatory support device further comprises a detector module coupled to first optical pressure sensor and the second optical pressure sensor. The detector module comprises at least one lens, and an image sensor configured to sense light received from the at least one lens. In one aspect, the at least one lens comprises a plano lens. In one aspect, the plano lens comprises a set of D-shaped lenses having curved edges facing each other. In one aspect, the at least one lens is configured to reduce spherical aberration in the light received from the first optical pressure sensor and the second optical pressure sensor. In one aspect, the at least one lens is configured to magnify a light signal incident on the at least one lens. In one aspect, a magnification factor of the at least one lens is at least 1.1 and less than 3. In one aspect, the magnification factor is at least 1.1 and less than 2. In one aspect, the magnification factor is less than 1.5. In one aspect, the magnification factor is less than 1.3. In one aspect, the at least one lens includes at least two lenses that collectively magnify the light signal incident on the at least one lens. In one aspect, the at least two lenses comprise a first lens having a first focal length and a second lens having a second focal length different from the first focal length. In one aspect, each of the first lens and the second lens is a D-shaped lens having a curved edge, and the curved edges of the first and second lenses are arranged to face each other.

In one aspect, the detector module further comprises a Fizeau arranged between the at least one lens and the image sensor. In one aspect, the image sensor comprises a two-dimensional image sensor. In one aspect, the at least one lens and the Fizeau are configured to collectively project the light received from the first and second optical pressure sensors as two lines on the two-dimensional image sensor. In one aspect, the two lines are two parallel lines. In one aspect, each of the two lines on the two-dimensional image sensor comprises an interferogram, the at least one hardware processor is further configured to determine based, at least in part, on light sensed by the image sensor, a first pressure measured at the first optical pressure sensor and a second pressure measured at the second optical pressure sensor by determining the first pressure and the second pressure based on a corresponding interferogram, and determining the differential pressure signal based, at least in part, on the first pressure signal and the second pressure signal comprises determining the differential pressure signal based on the first pressure and the second pressure.

DETAILED DESCRIPTION

Figure 1B:
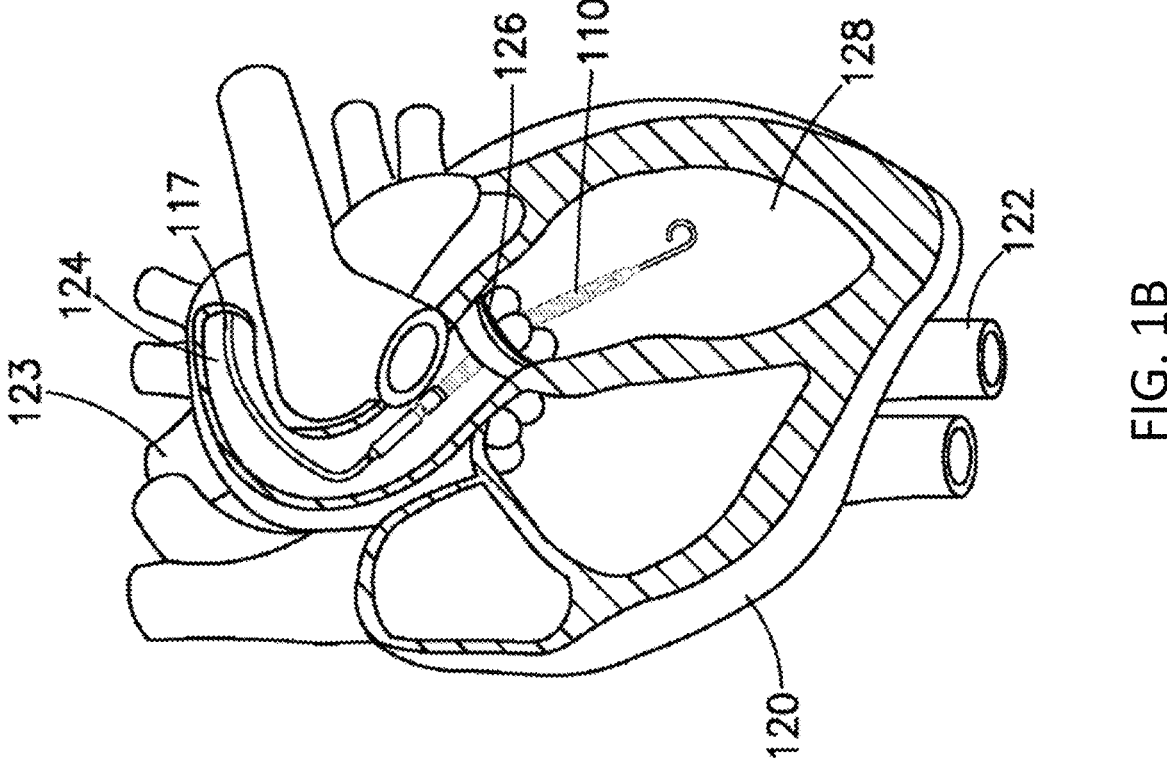
FIG. 1B illustrates the circulatory support device of FIG. 1A positioned within a heart of a patient.

A circulatory support device (also referred to herein as a "heart pump" or simply a "pump") may include a percutaneous, catheter-based device that provides hemodynamic support to the heart of a patient. As will be appreciated, for a heart pump to function properly, it should be positioned correctly in the heart of a patient, with an inlet portion of the pump located in the left ventricle and an outlet portion of the pump located in the aorta, thereby spanning the aortic valve of the patient's heart. As shown in FIG. 1A, a heart pump 110 may include a pigtail 111, an inlet area 112, a cannula 113, a pressure sensor 114, an outlet area 115, a motor housing 116, and/or a catheter tube 117. Pigtail 111 may assist with stabilizing heart pump 110 in the heart of a patient. It should be appreciated that some embodiments of heart pump 110 may not include pigtail 111 and heart pump 110 may be stabilized in other ways or not at all. During operation, blood may be drawn into one or more openings of inlet area 112, channeled through cannula 113, and expelled through one or more openings of outlet area 115 by a motor (not shown) disposed in motor housing 116. In some implementations, pressure sensor 114 may include a flexible membrane that is integrated into cannula 113. One side of pressure sensor 114 may be exposed to the blood pressure on the outside of cannula 113, and the other side may be exposed to the pressure of the blood inside of cannula 113. In some such implementations, pressure sensor 114 may generate an electrical signal proportional to the difference between the pressure outside cannula 113 and the pressure inside cannula 113. In some implementations, pressure sensor 114 may include an optical pressure sensor. Catheter tube 117 may provide one or more fluidic and/or electrical connections between heart pump 110 and one or more other devices of a ventricular support system, an example of which is shown in FIG. 1C.

Figure 1A:
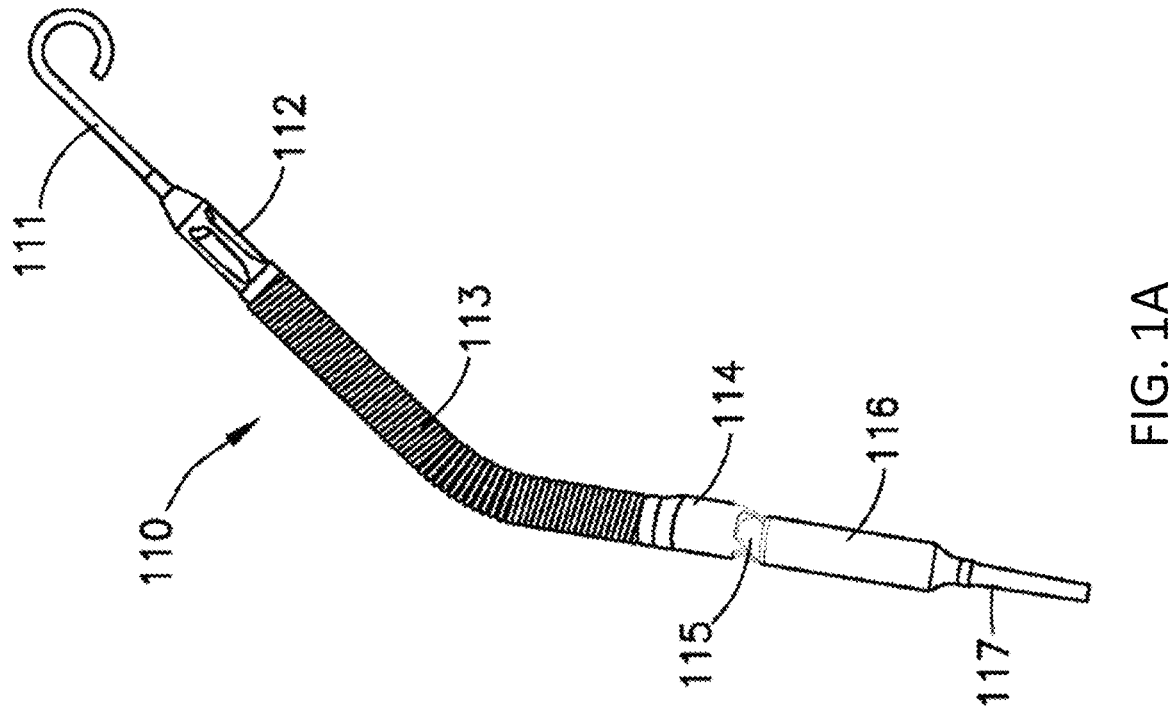
FIG. 1A shows an illustrative circulatory support device that may be used in accordance with some embodiments.

As shown in FIG. 1B, heart pump 110 may be positioned in a patient's heart 120. For example, heart pump 110 may be inserted percutaneously via the femoral artery 122 into the ascending aorta 124, across the aortic valve 126, and into the left ventricle 128. In other implementations, a heart pump may, for example, be inserted percutaneously via the axillary artery 123 into the ascending aorta 124, across the aortic valve 126, and into the left ventricle 128. In other implementations, a heart pump may, for example, be inserted directly into the ascending aorta 124, across the aortic valve 126, and into the left ventricle 128. During operation, heart pump 110 may entrain blood from the left ventricle 128 and expel blood into the ascending aorta 124. As a result, head pump 110 may perform some of the work normally done by the patient's heart 120. The hemodynamic effects of heart pumps may include an increase in cardiac output, improvement in coronary blood flow resulting in a decrease in left ventricle end-diastolic pressure, pulmonary capillary wedge pressure, myocardial workload, and oxygen consumption.

Figure 1C:
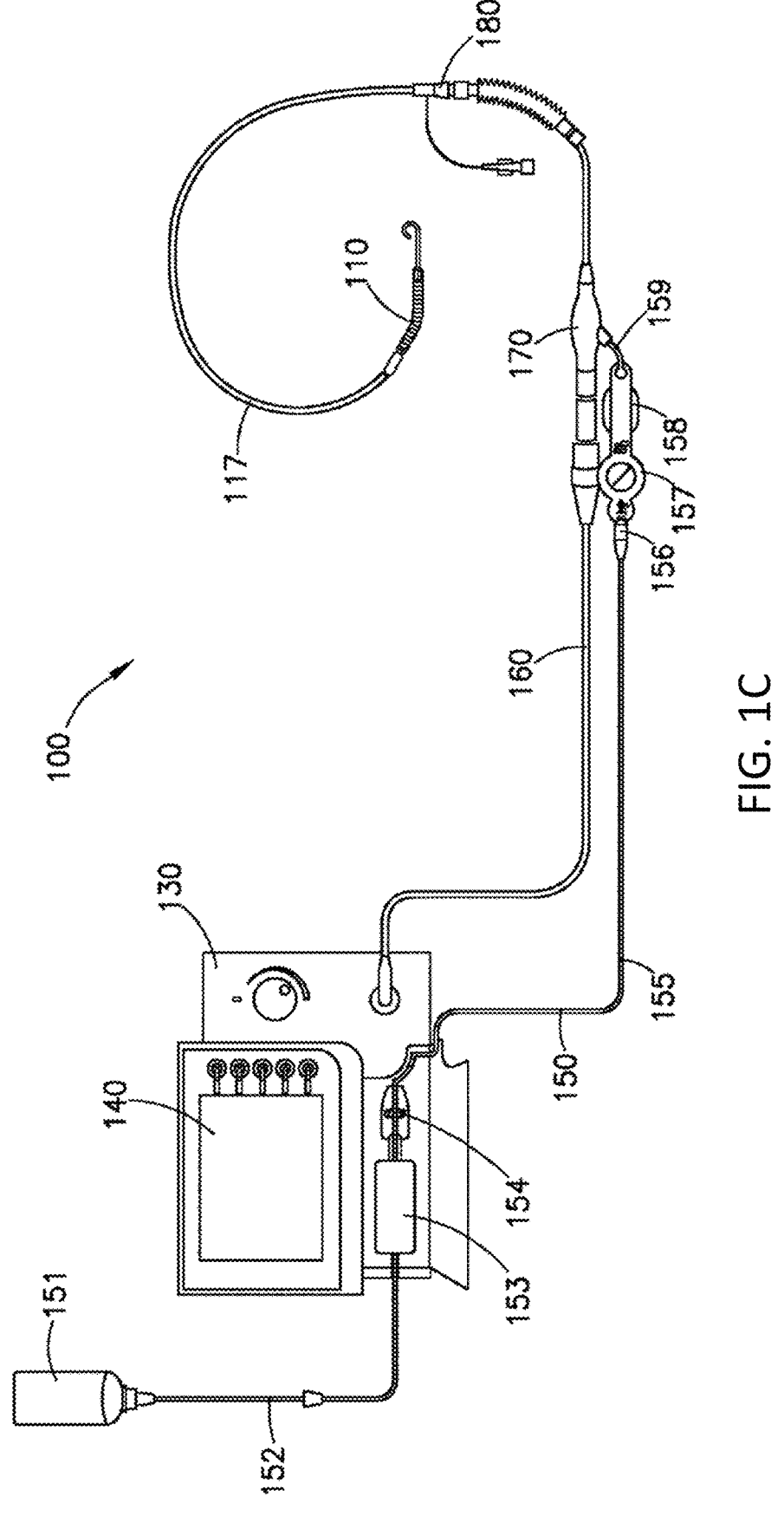
FIG. 1C illustrates a ventricular support system including the circulatory support device of FIG. 1A.

As shown in FIG. 1C, heart pump 110 may form part of a ventricular support system 100. Ventricular support system 100 also may include a controller 130 (e.g., an Automated Impella Controller®, referred to herein as "AIC," from ABIOMED, Inc., Danvers, Mass.), a display 140, a purge subsystem 1150, a connector cable 160, a plug 170, and a repositioning unit 180. As shown, controller 130 may include display 140. Controller 130 monitors and controls operation of heart pump 110. During operation, purge subsystem 150 may be configured to deliver a purge fluid to heart pump 110 through catheter tube 117 to prevent blood from entering the motor (not shown) within motor housing 116. In some implementations, the purge fluid is a dextrose solution (e.g., 5% dextrose in water with 25 or 50 IU/mL of heparin). Connector cable 160 may provide an electrical connection between heart pump 110 and controller 130. Plug 170 may connect catheter tube 117, purge subsystem 150, and connector cable 160. In some implementations, plug 170 includes a storage device (e.g., a memory) configured to store, for example, operating parameters to facilitate transfer of the patient to another controller if needed. Repositioning unit 180 may be used to reposition heart pump 110 in the patient's heart.

As shown, in some embodiments, the ventricular support system may include a purge subsystem 150 having a container 151, a supply line 152, a purge cassette 153, a purge disc 154, purge tubing 155, a check valve 156, a pressure reservoir 157, an infusion filter 158, and a sidearm 159. Container 151 may, for example, be a bag or a bottle. As will be appreciated, in other embodiments the ventricular support system may not include a purge subsystem. In some embodiments, a purge fluid may be stored in container 151. Supply line 152 may provide a fluidic connection between container 151 and purge cassette 153. Purge cassette 153 may control how the purge fluid in container 151 is delivered to heart pump 110. For example, purge cassette 153 may include one or more valves for controlling a pressure and/or flow rate of the purge fluid. Purge disc 154 may include one or more pressure and/or flow sensors for measuring a pressure and/or flow rate of the purge fluid. As shown, controller 130 may include purge cassette 153 and purge disc 154. Purge tubing 155 may provide a fluidic connection between purge disc 154 and check valve 156. Pressure reservoir 157 provides additional filling volume during a purge fluid change. In some implementations, pressure reservoir 157 includes a flexible rubber diaphragm that provides the additional filling volume by means of an expansion chamber. Infusion filter 158 helps prevent bacterial contamination and air from entering catheter tube 117. Sidearm 159 provides a fluidic connection between infusion filter 158 and plug 170.

Although shown as having separate purge tubing and connector cable, it will be appreciated that in some embodiments, the ventricular support system may include a single connector with both fluidic and electric lines connectable to the AIC.

During operation, controller 130 may be configured to receive measurements from pressure sensor 114 and purge disc 154 and to control operation of the motor (not shown) within motor housing 116 and purge cassette 153. As noted above, controller 130 may be configured to control and measure a pressure and/or flow rate of a purge fluid via purge cassette 153 and purge disc 154. During operation, after exiting purge subsystem 150 through sidearm 159, the purge fluid may be channeled through purge lumens (not shown) within catheter tube 1 and plug 170. Sensor cables (not shown) within catheter tube 117, connector cable 160, and plug 170 may provide an electrical connection between pressure sensor 114 and controller 130. Motor cables (not shown) within catheter tube 117, connector cable 160, and plug 170 may provide an electrical connection between the motor within motor housing 116 and controller 130. During operation, controller 130 may be configured to receive measurements from pressure sensor 114 through the sensor cables (e.g., optical fibers) and to control the electrical power delivered to the motor within motor housing 116 through the motor cables. By controlling the power delivered to the motor within motor housing 116, controller 130 is operable to control the speed of the motor within motor housing 116.

Various modifications can be made to ventricular support system 100 and one or more of its components. For instance, one or more additional sensors may be added to heart pump 100. In another example, a signal generator may be added to heart pump 100 to generate a signal indicative of the rotational speed of the motor within motor housing 116. As another example, one or more components of ventricular support system 100 may be separated. For instance, display 140 may be incorporated into another device in communication with controller 130 (e.g., wirelessly or through one or more electrical cables).

As described herein, a heart pump (e.g., heart pump 110) may include a pressure sensor 114 (e.g., an optical pressure sensor) configured to detect a pressure within the aorta of a patient's heart when the heart pump is properly positioned. The pressure signal sensed by pressure sensor 114 may be used, at least in part, to determine correct positioning of the heart pump within the patient's heart and/or to determine a blood flow rate through the heart pump when in operation. For instance, the pressure signal may be used in combination with a motor current signal received from a motor current sensor (not shown) and a set of stored values to determine a flow rate through the heart pump. The differential pressure across the aortic valve may also indirectly be determined based on the pressure signal measuring the pressure in the aorta and the set of stored values.

Figure 2:
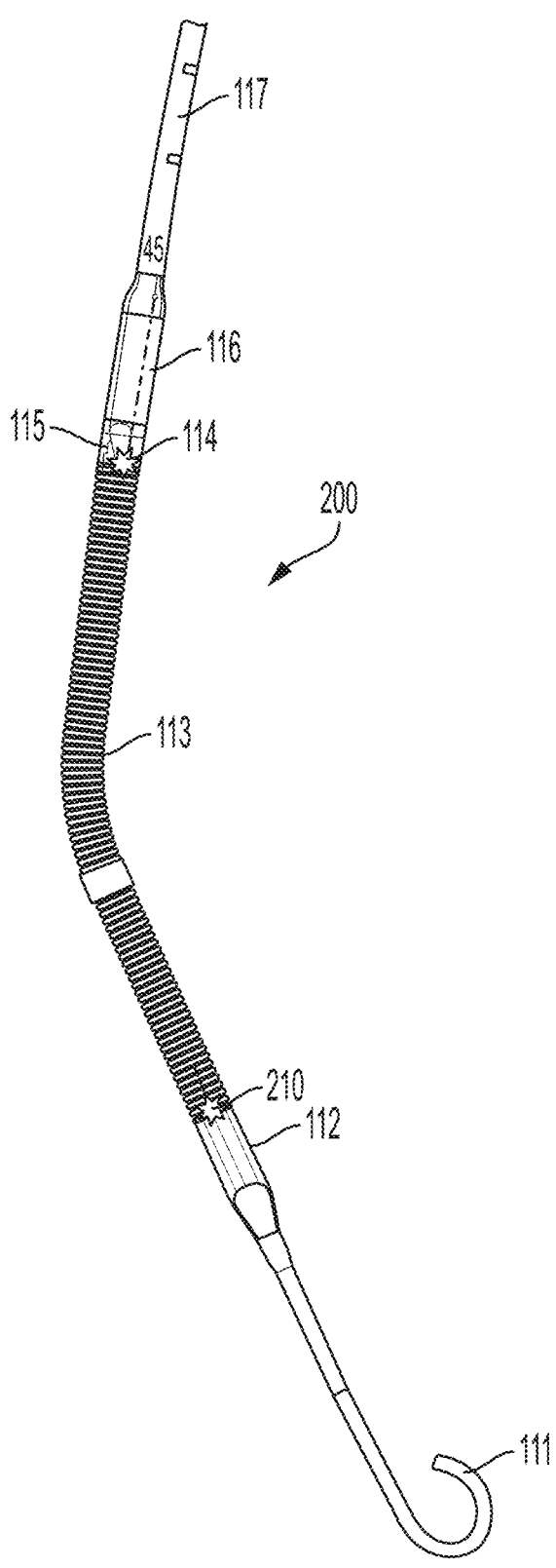
FIG. 2 illustrates a circulatory support device including a multi-channel optical pressure sensor in accordance with some embodiments.

The inventors have recognized and appreciated that it may be useful to incorporate one or more additional pressure sensors in heart pump 110, for example, to directly sense pressure in both the aorta and the left ventricle rather than having to infer the pressure in the left ventricle based on the pressure sensor signal sensed in the aorta, as discussed above. Use of multiple pressure sensors is also referred to herein as implementing a multi-channel pressure sensor. FIG. 2 illustrates an embodiment of heart pump 200 in which a second pressure sensor 210 is arranged near inlet area 112. When properly positioned within the heart of a patient, the second pressure sensor 210 may be configured to measure a pressure sensor signal used to determine a left ventricular blood pressure, in such implementations, additional sensor cables (e.g., optical fibers) may be disposed within catheter tube 117 to provide a connection between the second pressure sensor 210 and the controller (e.g., controller 130).

Figure 3:
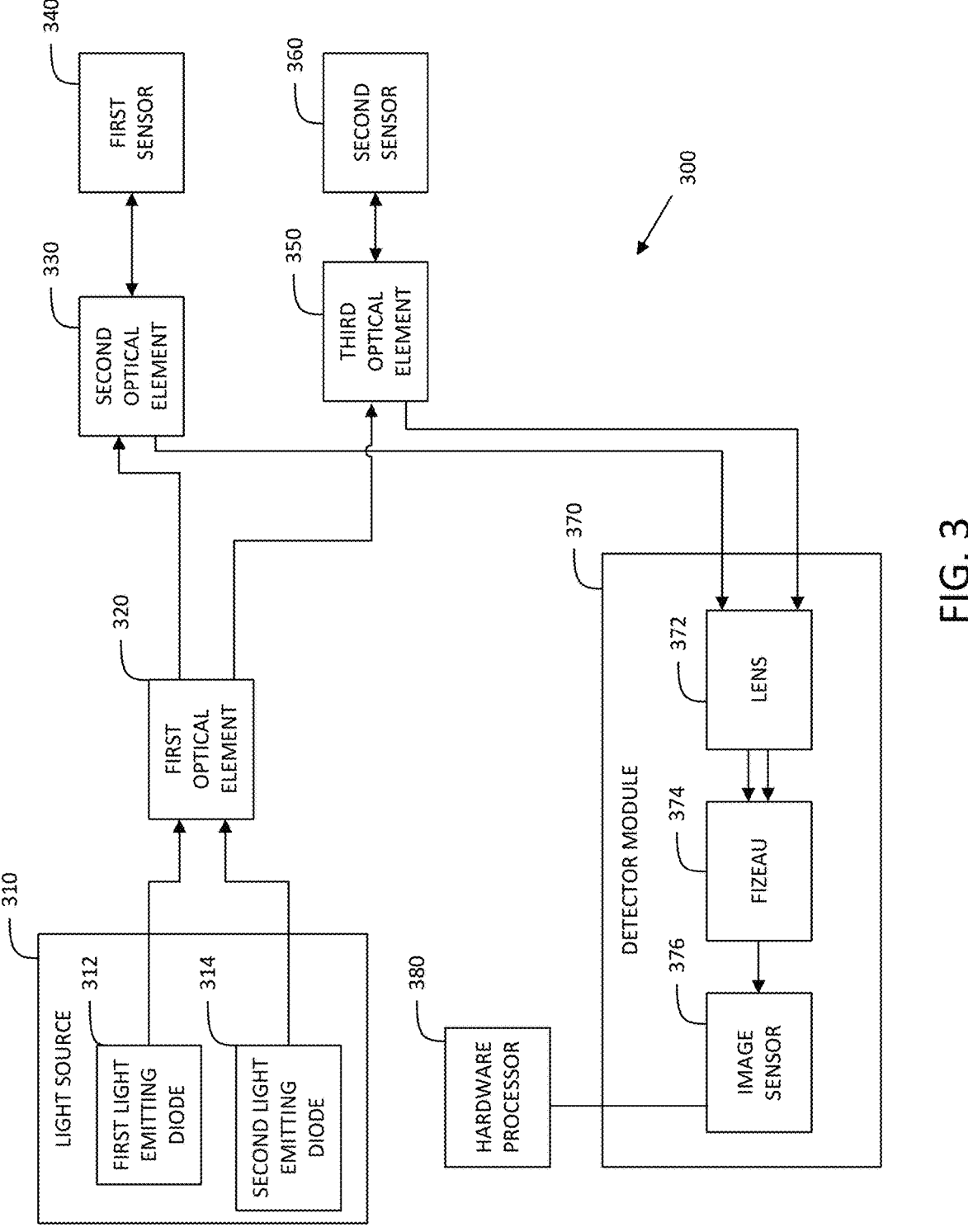
FIG. 3 illustrates components of a multi-channel optical pressure sensor system in accordance with some embodiments.

The inventors have recognized and appreciated that to accommodate multiple pressure sensors within a heart pump it may be useful to provide a lower power and/or smaller sensor than pressure sensors (e.g., including pressure sensor 114) used in some conventional heart pumps. Additionally, the use of optical-based pressure sensors may have advantages over electronic or other types of pressure sensors, including, but not limited to, their smaller size, their small or negligible pressure drift and their durability. FIG. 3 schematically illustrates a multi-channel pressure sensor system 300 designed in accordance with some embodiments of the present technology. System 300 includes light source 310 and multiple optical sensors (e.g., first sensor 340 and second sensor 360) coupled via optical fibers and one or more optical elements. In the example system 300, light source 310 includes two light emitting diodes (LEDs) (i.e., first LED 312 and second LED 314) configured to output light with different spectra. As described in more detail below, the spectrum of the light output from first LED 312 and second LED 314 may be selected such that their combined output has some characteristics similar to white light generated, for example, by a tungsten lamp. In some embodiments, the size of the LED may be smaller than 1 millimeter. Such characteristics may facilitate the use of lower-power LED light sources to perform multi-channel optical pressure sensing in a heart pump in accordance with the techniques described herein.

As shown, system 300 includes a plurality of optical elements arranged between light source 310 and the plurality of sensors (e.g., sensors 340, 360). A first optical element 320 is arranged to receive light from first LED 312 and second LED 314. In some embodiments, first optical element 320 is implemented as a splitter that mixes light from first LED 312 and second LED 314 and provides at its output, light to second optical element 330 and third optical element 350. The light provided as input to second optical element 330 and third optical element 350 may have a blended or "mixed" spectrum from the light output from first LED 312 and second LED 314 and may have half of the power as the light provided as input to first optical element 320 from light source 310. By mixing the light from first LED 312 and second LED 314, the first optical element provides light with a spectrum that has some characteristics in common with white light that may be produced with less-efficient (e.g., tungsten-based) light source. It should be appreciated that other types of light sources and/or optical components may alternatively be used to generate light for use with some embodiments. For instance, a single low power light source 310 configured to generate light having multiple spectra or a complex spectra having some characteristics in common with white light (e.g., light with a broad spectrum, such as a super broad LED) may alternatively be used. In such an embodiment, first optical element 320, which is configured to mix light from multiple light sources (e.g., LED 312 and LED 314) may not be needed, and the light output from the single light source may be provided via one or more optical fibers directly to second optical element 330 and third optical element 350.

In some embodiments, second optical element 330 may be implemented as a splitter that provides the mixed spectrum light output from first optical element 320 to first sensor 340. First sensor 340 may be configured as a reflective element such that at least some of the light provided to first sensor 340 is reflected back through second optical element 330, which provides the reflected light as input to detector module 370. Similarly, third optical element 350 may be configured as a splitter that provides the mixed spectrum light output from first optical element 320 to second sensor 360. Second sensor 360 may be configured as a reflective element such that at least some of the light provided to second sensor 360 is reflected back through third optical element 350, which provides the reflected light as input to detector module 370. In this way, the reflected light signals provided by the first sensor 340 and the second sensor 360 are further processed by components of detector module 370. In some embodiments, a first optical fiber coupled between the second optical element 330 and the detector module 370 and a second optical fiber coupled between the third optical element 350 and the detector module 370 may be coupled to the detector module 370 via a connector configured to arrange the first and second optical fibers in close proximity to each other.

As shown, detector module 370 may include one or more lenses 372 (e.g., a plano lens, an aspherical lens, a bi-convex lens, etc.), a Fizeau 374 and an image sensor 376. In some embodiments, lens 372 may be implemented as a pair of D-shaped lenses facing each other, as described in further detail herein. In some embodiments, lens 372 may be configured to provide magnification to optical signals transmitted through the lens 372. In some embodiments, the magnification may be provided by implementing lens 372 as a pair of asymmetrical D-shaped lenses facing each other as described in further detail herein. Lens 372 may be used to reduce spherical aberration, thereby enabling multiple channels of light reflected from the sensors to be separated in space and represented on the detector as two (or more) parallel or nearly parallel lines with limited cross-talk between them. Light received by lens 372 is provided as input to Fizeau 374. Fizeau 374 may be implemented as two reflective mirrors having arranged between them a space varying dielectric layer. Light entering Fizeau 374 may resonate at a particular place on the space varying dielectric layer to create beams of light that are captured by the detector 376, as shown for example, in FIG. 7A. In some embodiments, image sensor 376 may be configured as a two-dimensional image sensor upon which multiple channels of light are detected corresponding to an interferogram of the reflected light signals from the first sensor 340 and the second sensor 360. System 300 may further include at least one hardware processor 380 configured to analyze signals captured by image sensor 376 to, for example, determine the pressure sensed by each of the first sensor 340 and the second sensor 360 based on the interferogram signals captured by the image sensor 376. In some embodiments, at least one hardware processor 380 may be implemented as part of controller 130 as described above in connection with FIG. 1C.

Figure 4:
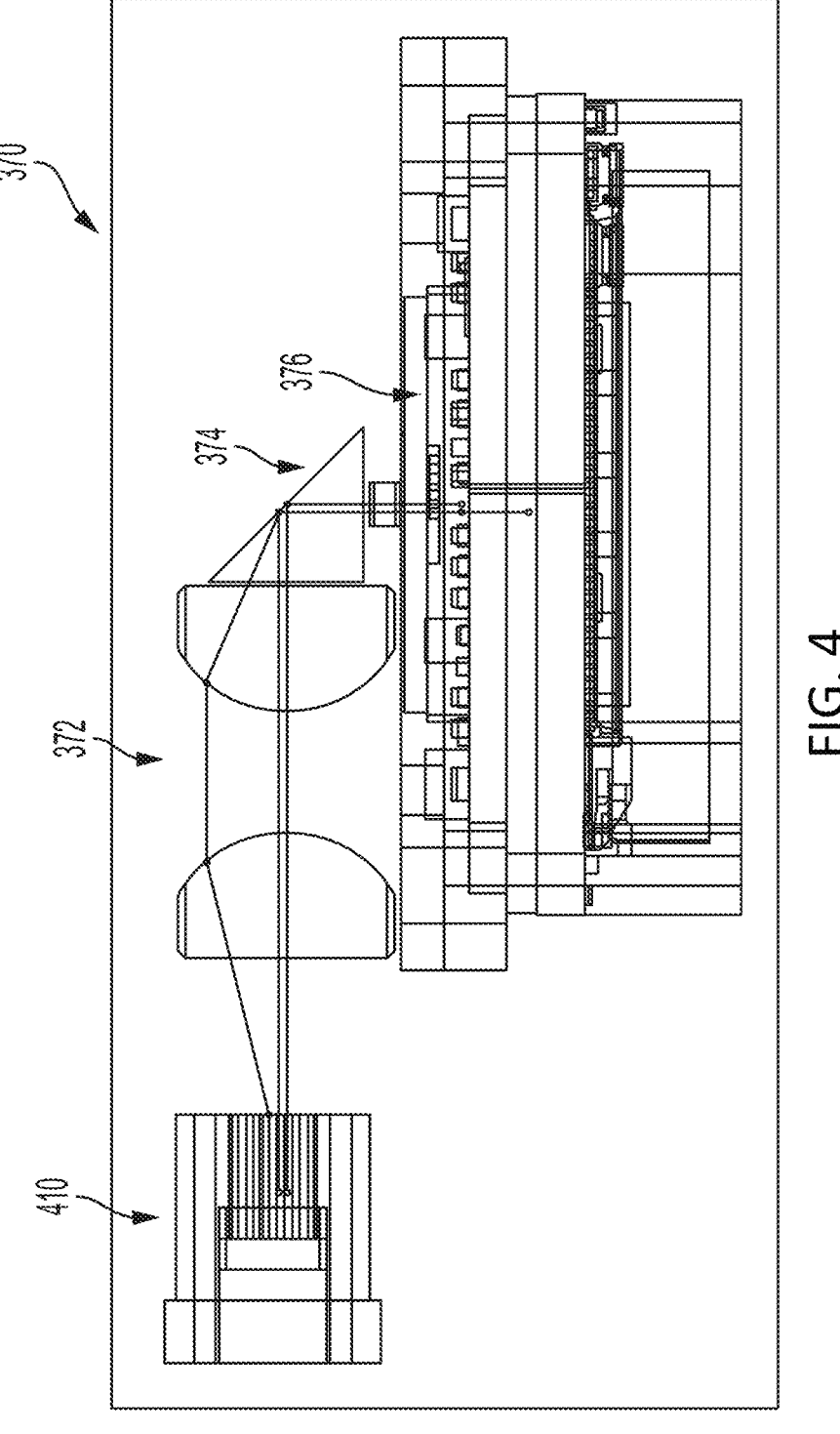
FIG. 4 schematically illustrates a detector module for a multi-channel optical pressure sensor system in accordance with some embodiments.

FIG. 4 schematically illustrates an arrangement of components of detector module 370 in accordance with some embodiments. As shown detector module 370 includes connector 410 configured to receive optical fibers from second optical element 330 and third optical element 350 as described above in connection with FIG. 3. Connector 410 may be configured to arrange the incoming optical fibers in close proximity to one another. Two beams of light output from connector 410 are provided to lens 372 to focus the light on Fizeau 374, which redirects the light onto a surface of the image sensor 376. In some embodiments, connector 410 is moveable in a plane parallel to lens 372 to adjust a focus of the light beams on image sensor 376. As shown, lens 372 may be implemented as a set of D-shaped lenses having their curved edges oriented toward each other. Lens 372 may be configured to reduce spherical aberration that would be present if, for example, a rod lens was used.

Figure 5:
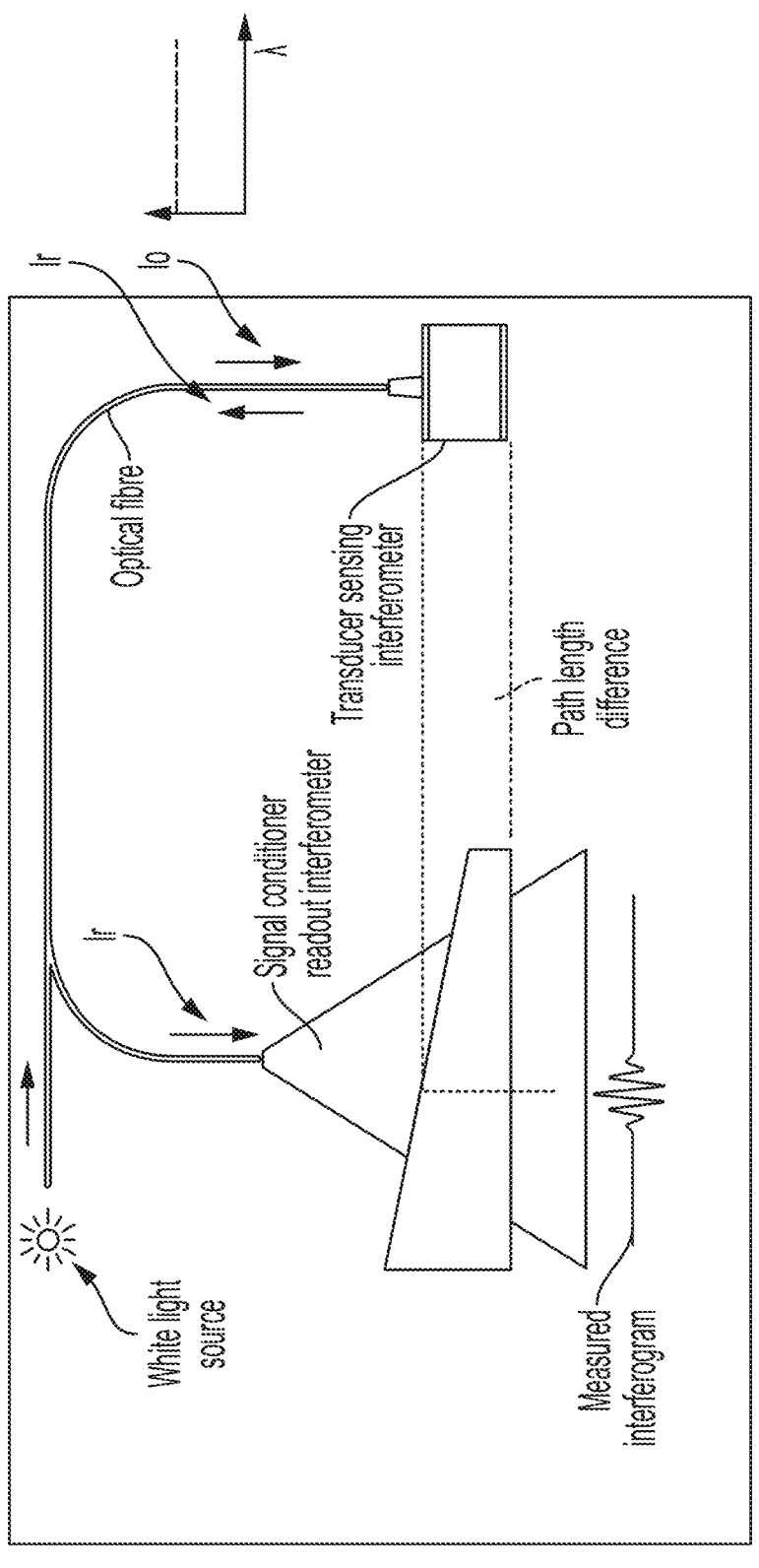
FIG. 5 schematically illustrates a process for generating an interferogram using a single-channel optical pressure sensor system.

FIG. 5 schematically illustrates a process for performing interferometry using an optical system such as those described herein. In the example of FIG. 5, a white light source (e.g., a tungsten lamp) is used as a light source (e.g., light source 310 in FIG. 3). However, it should be appreciated that other light sources (e.g., LEDs 312, 314) may alternatively be used. As shown, the light generated by the source is provided via an optical fiber as incident light $I_0$ to the sensor (e.g., sensor 340 or sensor 360 in FIG. 3). As shown, the sensor may be implemented as a transducer sensing interferometer. Reflected light $I_r$ is provided to a detector module (e.g., detector module 370) that includes an optical wedge (e.g., Fizeau 374), which is used to produce an interferogram signal (e.g., on image sensor 376). A center peak of the interferogram signal may be tracked and/or otherwise used to determine a pressure value sensed by the sensor.

As discussed herein, the inventors have recognized and appreciated that some conventional white light sources generate a considerable amount of heat and use a large amount of power, which limits their use in certain implementations including as a light source for a multi-channel optical pressure sensor in a heart pump. Accordingly, in some embodiments, one or more lower power light sources may be used to provide light having some characteristics similar to white light. For instance, as described above in connection with system 300 shown in FIG. 3, two LED sources configured to generate light having different spectra may be used.

Figures 6A, 6B:
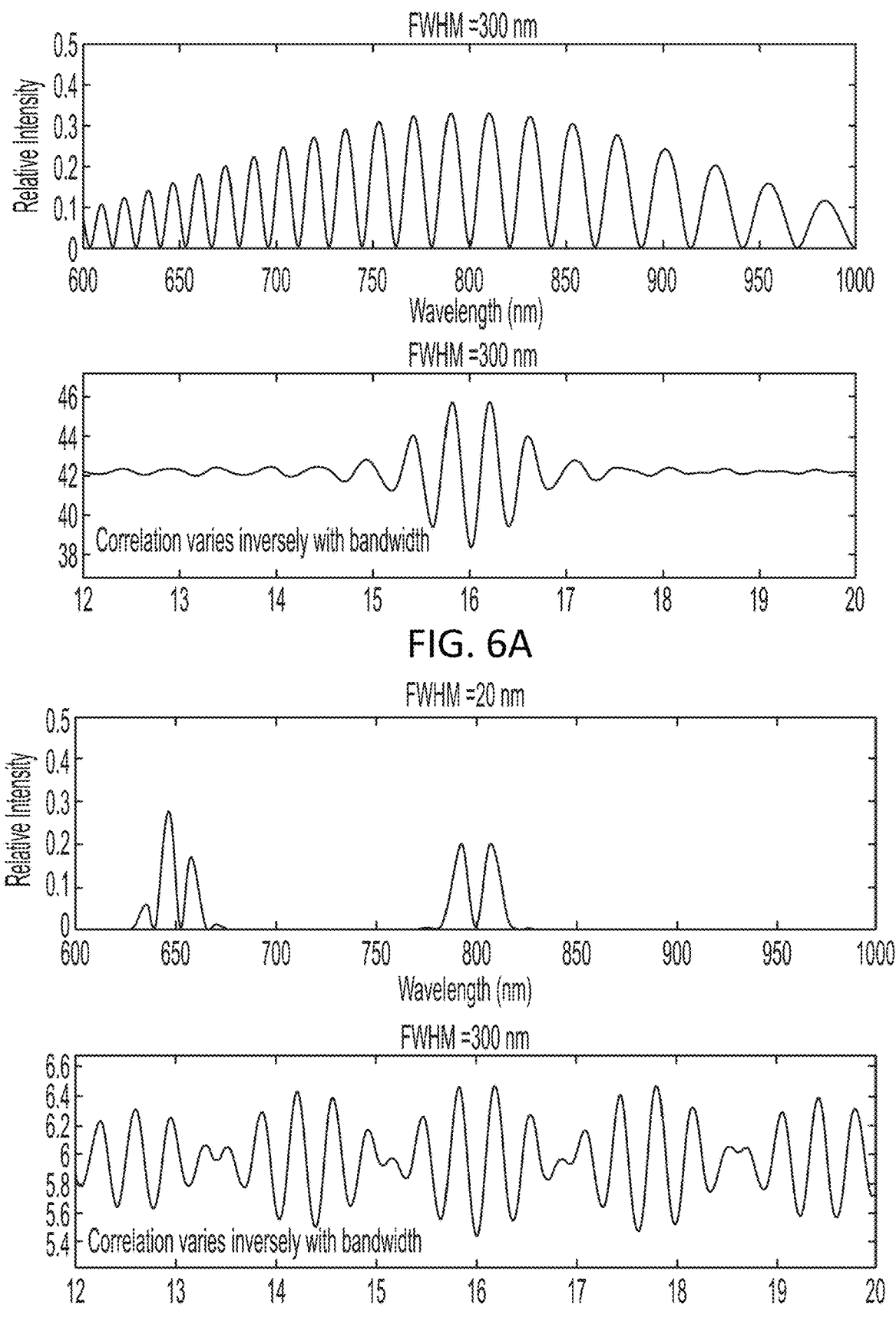
FIG. 6A illustrates a spectrum (top) and an interferogram signal (bottom) of a broadband white light source that may be used in the single-channel optical pressure sensor system of FIG. 5.
FIG. 6B illustrates a spectrum (top) and an interferogram signal (bottom) of a dual LED light source that may be used in a multi-channel optical pressure sensor system in accordance with some embodiments.

FIG. 6A shows plots of the spectrum of light output by a white light source (top plot) and the corresponding interferogram signal (bottom plot) recorded using the white light source. As shown, a conventional white light source has a broadband spectrum, which produces an interferogram signal with a well-defined central region with small side lobes. Such an interferogram signal is ideal for determining a pressure sensed by the coupled optical pressure sensor. FIG. 6B shows plots of the spectrum of light output by two narrowband LED sources (top plot) and the corresponding interferogram signal (bottom plot) recorded using the two LED sources. The spectrum of light produced by a first LED source may have a lower peak wavelength (e.g., in the range of 550-650 nm) and the spectrum of light produced by a second LED source may have a higher peak wavelength (e.g., the range of 800-900 nm). In some embodiments, the spectrum of light produced by the first LED source has a peak wavelength in the range of 550-610 nm and the spectrum of light produced by the second LED source has a peak wavelength in the range of 820-850 nm. In some embodiments, the peak wavelength of the first LED source is ⅘ of the peak wavelength of the second LED source.

Figure 6C:
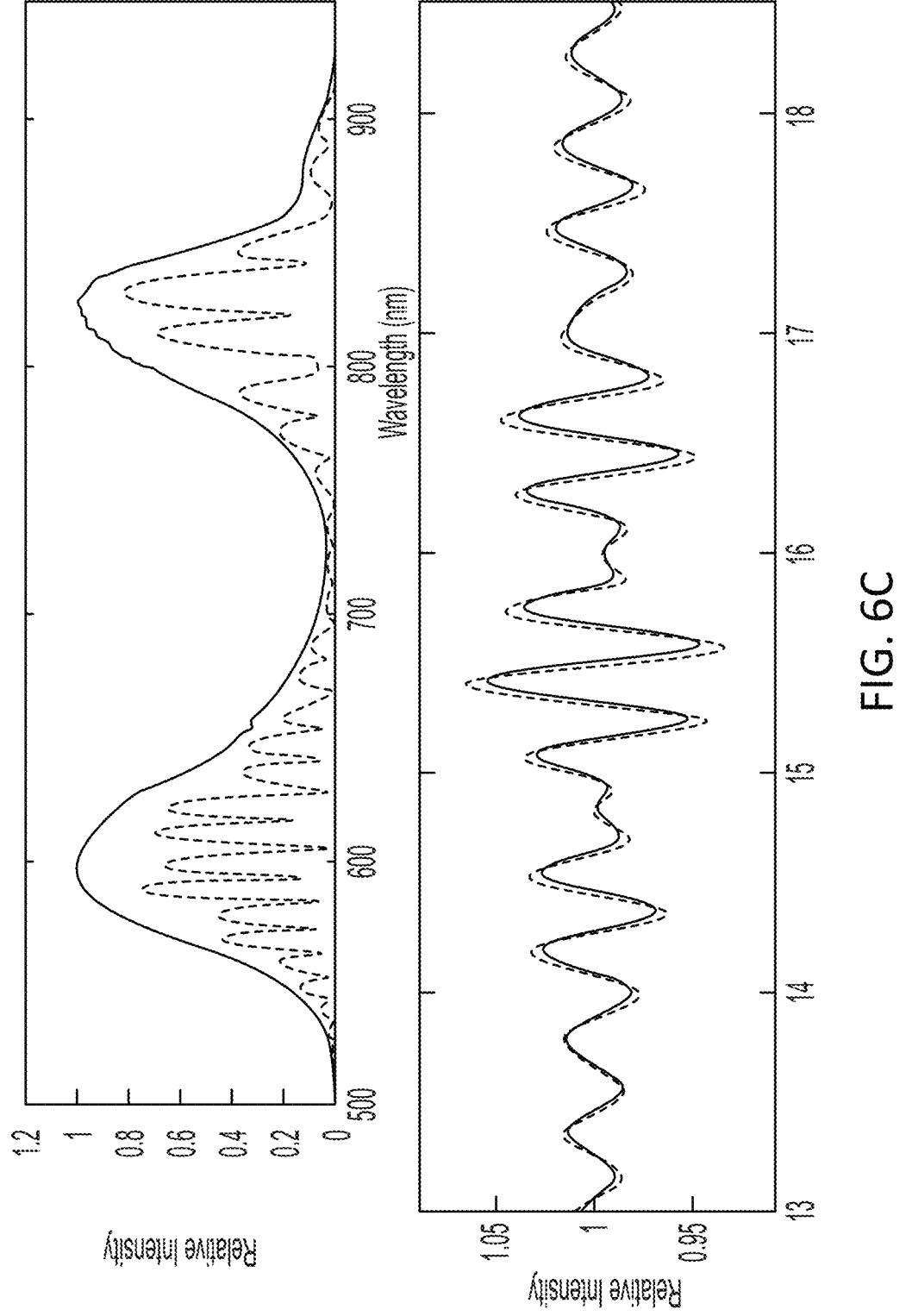
FIG. 6C illustrates a spectrum (top) and an interferogram signal (bottom) of a dual broad spectrum LED light source that may be used in a multi-channel optical pressure sensor system in accordance with some embodiments.

As shown in the bottom plot of FIG. 6B, the interferogram signal produced using the two narrowband LED sources has some characteristics similar to the interferogram signal produced using the broadband white light source shown in FIG. 6A. For instance, the interferogram signal shown in FIG. 6B has a central portion similar to central portion of the interferogram signal shown in FIG. 6A, and a lateral envelope that distinguishes the central region from other portions of the signal. When the lateral envelope adjacent to the central portion of the signal falls off sufficiently enough to enable tracking the central portion of the signal relative to the other portions of the signal, the interferogram signal shown in 6B can be used in a similar manner to the interferogram signal shown in FIG. 6A and as described above in connection with the process shown in FIG. 5. FIG. 6C illustrates an interferogram produced by two LEDs have a broader spectrum. As shown in the bottom plot of FIG. 6C, the interferogram signal produced by the two broad spectrum LED sources is closer to an interferogram produced by a tungsten lamp. In the some embodiments, the lateral envelopes of the interferogram signal may be attenuated substantially. Accordingly, some embodiments mimic the use of a broadband white light source by using multiple narrowband and lower power LED sources, which when used in combination, generate an interferogram signal that can be used in a multi-channel optical pressure sensor (e.g., for a heart pump). In some embodiments, one or more characteristics (e.g., amplitude, position) of the center peak of the central portion of the interferogram signal may be used to determine a pressure value sensed by a corresponding pressure sensor associate with the interferogram signal. It should be appreciated that in some embodiments, more than two light sources (e.g., LEDs) may be used, and embodiments are not limited in this respect. Accordingly, although a two-channel optical pressure sensor system is shown and described herein, any multi-channel (e.g., two or more channels) optical pressure sensor system may be implemented using techniques similar to those described herein. More than two light sources may be beneficial in embodiments when more than two channels are used, such that the power of the light signal provided to each of the sensors is sufficient to generate reliable interferogram signals.

Figures 7A, 7B:
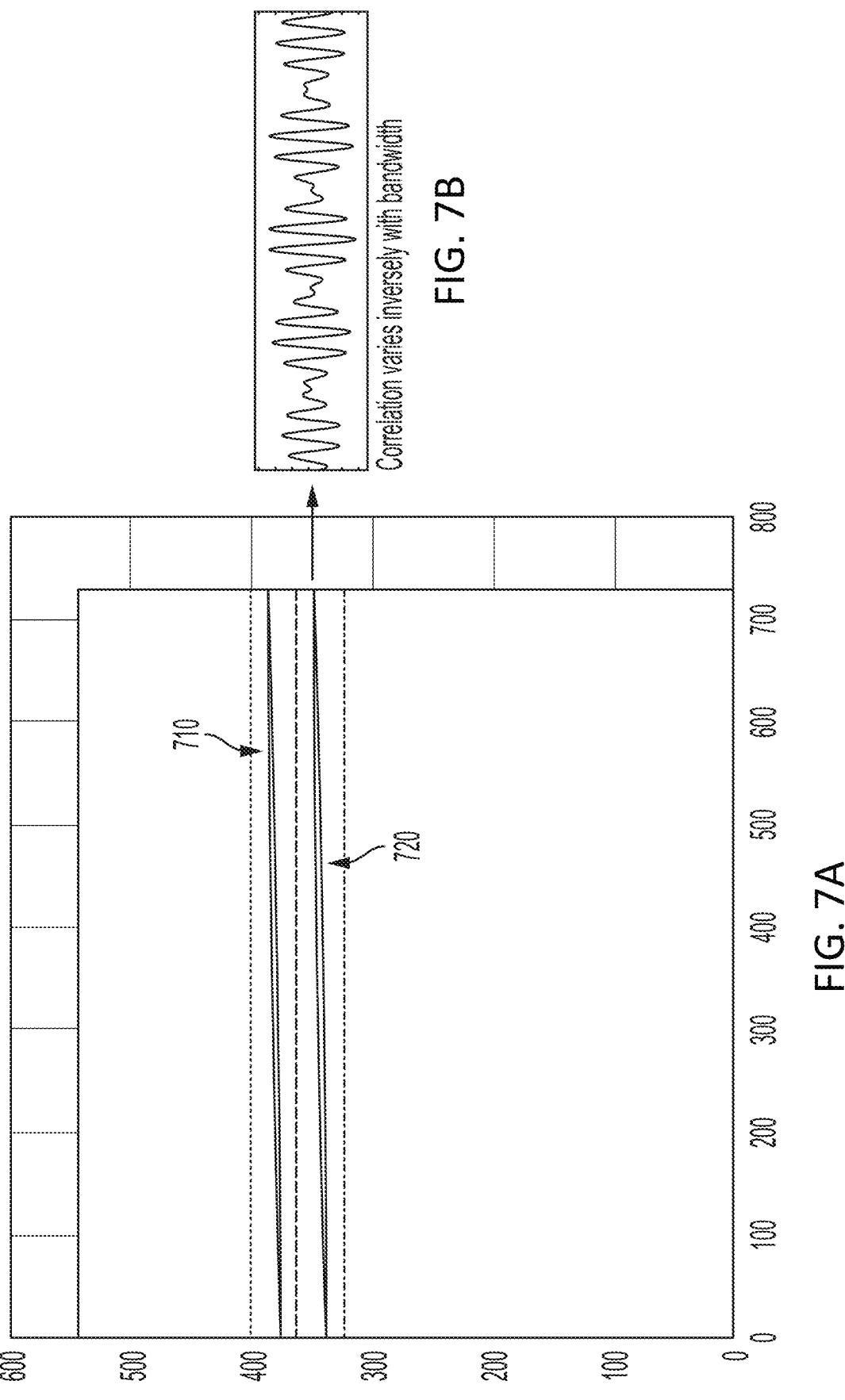
FIG. 7A illustrates a display of interferogram signals recorded using a two-dimensional image sensor of a multi-channel optical pressure sensor system in accordance with some embodiments.
FIG. 7B illustrates an interferogram signal extracted from the image sensor data shown in FIG. 7A.

FIG. 7A illustrates a display of an image representing the interferogram signals captured by a two-dimensional image sensor (e.g., image sensor 376 shown in FIG. 3) in accordance with some embodiments. As shown, the interferogram signal captured by the image sensor for each of the corresponding optical sensors is represented as a line. For instance, a first interferogram signal corresponding to reflected light from sensor 340 may be represented as line 710 and a second interferogram signal corresponding to reflected light from sensor 360 may be represented as line 720. As described herein, the components of the detector module may enable the interferogram signals represented as lines 710 and 720 to be spatially distinguishable and separable (e.g., with no or limited cross-talk). It should be appreciated that only a small portion of the image sensor shown in FIG. 7A is shown as being utilized, which demonstrates the feasibility of using more than two channels, if desired, according to the techniques described herein. For instance, in some embodiments, up to 6 channels, 8 channels, or 10 channels may be used. The intensity of the interferogram signal may be extracted from the captured image sensor signals into an interferogram signal as shown in FIG. 7B. Based, at least in part, on the extracted interferogram signal, a pressure sensed by the corresponding sensor may be determined, as described above.

Figure 8A:
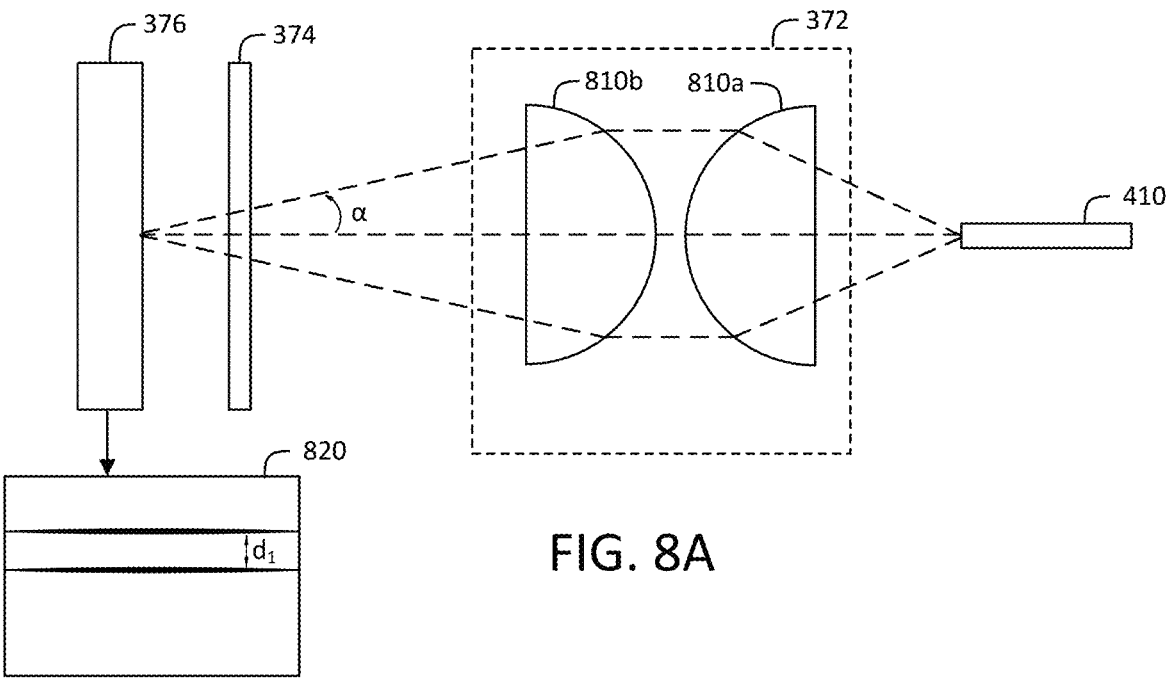
FIG. 8A schematically illustrates a lens design for a detector module that includes a symmetric pair of D-shaped lenses in accordance with some embodiments.

FIG. 8A schematically illustrates components of a detector module that may be used to detect an interferogram signal associated with an optical pressure sensor described in accordance with some embodiments. Similar to the detector module 370 shown in FIG. 4, the detector module shown in FIG. 8A may include a lens 372 configured to receive one or more beams of light (e.g., two beams of light for the dual optical channel detector design shown in FIG. 4) from an optical connector 410. Lens 372 may be configured to focus the light on Fizeau 374, which may redirect the light onto a surface of the image sensor 376.

The Fizeau 374 may be adjustable so that its cavity length range can be tuned to the cavity length range of the sensing interferometer which may change over time. Tuning the total range of the Fizeau to fit with the total range of the sensing interferometer may produce a maximum detected signal on the image sensor 376. For example, the Fizeau 374 may have a spatially varying cavity length between 14000 and 19000 nm and the sensing interferometer may have a cavity length of 15000 nm. In such an instance, the position along the Fizeau 374 where the cavity length of the Fizeau is equal to 15000 nm may produce a maximum interferometer signal on the image sensor 376. The inventors have recognized and appreciated that the cavity length of the Fizeau may depend, at least in part, on an angle through which an incident light beam travels through the interferometer. For example, as the angle increases, the cavity length may change, such that for a certain point on the Fizeau 374 there may be some incident light energy perpendicular to the Fizeau (e.g., at 0° or 90°) and some incident light energy at an angle. Due to incident light energy arriving at different angles, the resulting interferogram signal observed by the sensor 376 may correspond to a summation of all of the signals across the angle range, which may reduce the contrast of the sensed signal.

Similar to the lens design shown in FIG. 4, the design of lens 372 shown in FIG. 8A may be implemented as a set of D-shaped lenses having their curved edges oriented toward each other. In the example of FIG. 8A, the set of D-shaped lenses includes two symmetrical lenses 810a, 810b (e.g., lenses having the same focal length) such that the maximum incident angle of the light beams received by lens 810a from connector 410 is the same as the maximum angle of the light beams exiting the lens 810b. The maximum attack angle (i.e., the maximum angle of light energy incident on sensor 376) is indicated in the lens design of FIG. 8A as α. The inventors have recognized and appreciated that reducing the maximum attack angle α may increase the contrast of the signal redirected by the Fizeau 374 onto the sensor 376. In some embodiments described herein, the maximum attack angle α of the light energy output from the lens 372 may be reduced by magnifying the optical signal transmitted through lens 372.

The acceptance angle of the light beam output from the connector 410 and received by the lens 372 may be generally fixed without modification of the arrangement and/or orientation of optical fibers within the connector 410. Some conventional solutions to reduce the acceptance angle include bending the optical fiber to cutoff some of the modes of the optical signal. However, such techniques also reduce the overall energy in the signal, which may not be desirable in some applications for which the amount of energy in the light signal may be small. Rather than reducing the energy in the light energy provided as input to the lens 372, some embodiments disclosed herein reduce the maximum attack angle α by using a lens 372 that magnifies the optical signal passed through the lens 372 (e.g., by selecting a lens or combination of lenses having appropriate focal length characteristics). For a single-channel optical device in which a single line on the sensor 376 is to be generated (and therefore cross-talk between lines on the sensor 376 need not be considered), lens 372 may be configured using a single lens that provides magnification of the optical signal received from the connector 410. In a multi-channel optical device in which multiple lines on the sensor 376 are to be generated (and therefore where cross-talk between lines on the sensor 376 may be important to distinguish the multiple interferogram signals), examples of which are described herein, lens 372 may be configured using multiple lenses that collectively provide magnification of the incident optical signal.

Figure 8B:
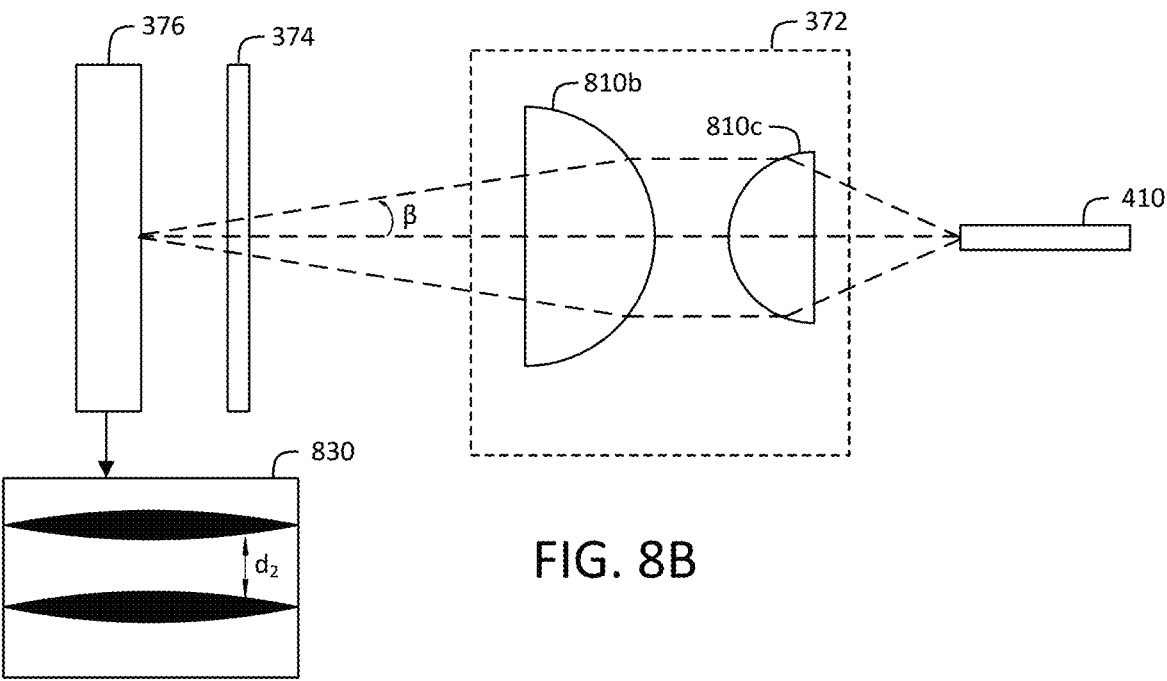
FIG. 8B schematically illustrates an alternate lens design for a detector module that includes an asymmetric pair of D-shaped lenses in accordance with some embodiments.

FIG. 8B schematically illustrates a detector module that includes a lens 372 configured to perform magnification of an optical signal received from connector 410 in accordance with some embodiments. As shown in FIG. 8B, lens 372 may be implemented as a set of asymmetric lenses 810b, 810c that have different focal lengths. Collectively, the set of lenses 810b, 810c may provide magnification of the optical signal received from connector 410, which in turn provides an optical signal at the output of lens 810b that has a reduced maximum attack angle β relative to the configuration shown in FIG. 8A, in which symmetrical lenses 810a, 810b are used (i.e., β<α). For example, if the focal length of lens 810b is selected to be 7.8 and the focal length of lens 810c is selected to be 5.5, the magnification factor of the lens 372 would be 7.8/5.5=1.4. By decreasing the maximum attack angle β, the contrast (e.g., peak-to-peak amplitude/average amplitude) of the interferometer signal is improved relative to when a larger maximum attack angle α is used.

Although configuring lens 372 to have higher amounts of magnification decreases the maximum attack angle β, thereby improving the contrast of the signal, configuring lens 372 to provide too much magnification may have some undesirable consequences with respect to the signal captured by the sensor 376. FIG. 7A illustrates an example of an image representing interferogram signals captured by a two-dimensional image sensor (e.g., image sensor 376 shown in FIG. 3) in accordance with some embodiments in which the detector module includes a lens 372 configured with a pair of symmetric lenses as shown in FIG. 8A. FIG. 8A schematically illustrates an image 820 of a two-dimensional image sensor in which two lines corresponding to interferogram signals for two channels of a multi-channel optical pressure sensor are separated by a distance $d_1$. FIG. 8B schematically illustrates an image 830 of a two-dimensional image sensor in which two lines corresponding to interferogram signals for two channels of a multi-channel optical pressure sensor that have been magnified using lenses 810b, 810c are separated by a distance $d_2$. As can be observed by comparing images 820 and 830, magnification of the optical signals using the lens design of FIG. 8B results in a larger number of pixels used to represent each of the interferogram signals on the sensor 376 compared to using the lens design shown in FIG. 8A. By using additional pixels to represent the magnified interferogram signals, the processing resources needed to process the captured signals (e.g., using hardware processor 380 shown in FIG. 3) may be increased at higher magnifications relative to embodiments in which less magnification is used. Additionally, the distance between the two interferogram signals may also be magnified (i.e., $d_2>d_1$), which may limit the number of additional channels of information that can be captured by the sensor 376 without increasing its size. As should be appreciated, selection of optimal components for lens 372 that increase magnification to improve contrast of the interferogram signals while reducing the spread of the detected signals on the sensor 376 may be determined based on a particular application and/or Fizeau design.

The inventors have recognized that configuring lens 372 to have a relatively small amount of magnification (e.g., 1.2×, 1.3×, 1.4×, 1.5×) may provide sufficient magnification to improve contrast while controlling the pixel spread of the interferogram signals on the sensor 376. For example, the pixel spread of the interferogram signals captured by sensor 376 may be controlled within reasonable bounds for some applications including a multi-channel optical pressure sensor as described herein by selecting a suitable magnification factor for lens 372. In some embodiments, a magnification factor of lens 372 may be greater than 1.1, greater than 1.2, greater than 1.3, greater than 1.4, or greater than 1.5. In some embodiments, the magnification factor of lens 372 may be less than 3, less than 2.5, less than 2, less than 1.5, less than 1.4, less than 1.3 or less than 1.2. In some embodiments, the magnification factor may be within any of the aforementioned ranges. For example, the magnification factor may be greater than 1.1 and less than 2, greater than 1.1 and less than 1.5, greater than 1.2 and less than 1.4, etc.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A multi-channel optical pressure sensor, comprising:
   at least one light-emitting diode (LED), wherein the at least one LED comprises a first LED configured to generate first light having a first spectrum and a second LED configured to generate second light having a second spectrum, the first spectrum having a peak wavelength in a range of 550-670 nm and the second spectrum having a peak wavelength in a range of 800-900 nm;
   a plurality of sensors including a first sensor coupled to the at least one LED via at least one first optical fiber and a second sensor coupled to the at least one LED via at least one second optical fiber;
   a detector module coupled to first sensor and the second sensor, the detector module comprising:
      at least one lens; and
      an image sensor configured to sense light received from the at least one lens; and
   at least one hardware processor configured to determine based, at least in part, on the light sensed by the image sensor, a first pressure measured at the first sensor and a second pressure measured at the second sensor.

2. The sensor of claim 1, wherein the first LED and/or the second LED is smaller than 1 mm.

3. The sensor of claim 1, further comprising:
   a first optical element arranged between the at least one LED and the plurality of sensors, the first optical element configured to:
      receive the first light and the second light; and output third light and fourth light, each of the third light and fourth light having a third spectrum.

4. The sensor of claim 3, further comprising:
a second optical element coupled to the first optical element, the first sensor, and the detector module; and
a third optical element coupled to the first optical element, the second sensor, and the detector module.

5. The sensor of claim 4, wherein:
the second optical element is configured to provide first reflected light from the first sensor to the detector module, and
the third optical element is configured to provide second reflected light from the second sensor to the detector module.

6. The sensor of claim 1, wherein the at least one lens comprises a plano lens.

7. The sensor of claim 1, wherein the at least one lens is configured to magnify a light signal incident on the at least one lens.

8. The sensor of claim 7, wherein the at least one lens includes at least two lenses that collectively magnify the light signal incident on the at least one lens.

9. The sensor of claim 1, wherein the detector module further comprises a Fizeau arranged between the at least one lens and the image sensor.

10. The sensor of claim 9, wherein the image sensor comprises a two-dimensional image sensor.

11. A circulatory support device, comprising:
a rotor;
a motor configured to drive rotation of the rotor at one or more speeds;
a first optical pressure sensor configured to detect a first pressure signal;
a second optical pressure sensor configured to detect a second pressure signal; and
at least one hardware processor configured to:
determine a differential pressure signal based, at least in part, on the first pressure signal and the second pressure signal.

12. The circulatory support device of claim 11, wherein the at least one hardware processor is further configured to determine a flow rate through the circulatory support device based, at least in part, on the differential pressure signal.

13. The circulatory support device of claim 11, further comprising:
a first light emitting diode (LED) coupled to the first optical pressure sensor and the second optical pressure sensor, the first LED being configured to generate first light having a first spectrum; and
a second LED coupled to the first optical pressure sensor and the second optical pressure sensor, the second LED being configured to generate second light having a second spectrum.

14. A multi-channel optical pressure sensor, comprising:
at least one light-emitting diode (LED);
a plurality of sensors including a first sensor coupled to the at least one LED via at least one first optical fiber and a second sensor coupled to the at least one LED via at least one second optical fiber;
a detector module coupled to first sensor and the second sensor, the detector module comprising:
at least one lens, wherein the at least one lens comprises a plano lens; and an image sensor configured to sense light received from the at least one lens; and
at least one hardware processor configured to determine based, at least in part, on the light sensed by the image sensor, a first pressure measured at the first sensor and a second pressure measured at the second sensor.

15. The sensor of claim 14, wherein the plano lens comprises a set of D-shaped lenses having curved edges facing each other.

16. A multi-channel optical pressure sensor, comprising:
at least one light-emitting diode (LED);
a plurality of sensors including a first sensor coupled to the at least one LED via at least one first optical fiber and a second sensor coupled to the at least one LED via at least one second optical fiber;
a detector module coupled to first sensor and the second sensor, the detector module comprising:
at least one lens, wherein the at least one lens includes at least two lenses configured to collectively magnify a light signal incident on the at least one lens; and
an image sensor configured to sense light received from the at least one lens; and
at least one hardware processor configured to determine based, at least in part, on the light sensed by the image sensor, a first pressure measured at the first sensor and a second pressure measured at the second sensor.

17. The sensor of claim 16, wherein the at least two lenses comprise a first lens having a first focal length and a second lens having a second focal length different from the first focal length.

18. A multi-channel optical pressure sensor, comprising:
at least one light-emitting diode (LED);
a plurality of sensors including a first sensor coupled to the at least one LED via at least one first optical fiber and a second sensor coupled to the at least one LED via at least one second optical fiber;
a detector module coupled to first sensor and the second sensor, the detector module comprising:
at least one lens, wherein the at least one lens includes at least two lenses configured to collectively magnify a light signal incident on the at least one lens;
an image sensor configured to sense light received from the at least one lens, wherein the image sensor comprises a two-dimensional image sensor; and
a Fizeau arranged between the at least one lens and the image sensor; and
at least one hardware processor configured to determine based, at least in part, on the light sensed by the image sensor, a first pressure measured at the first sensor and a second pressure measured at the second sensor.

19. The sensor of claim 18, wherein the at least one lens and the Fizeau are configured to collectively project the light received from the first and second sensors as two lines on the two-dimensional image sensor.

20. The sensor of claim 19, wherein each of the two lines on the two-dimensional image sensor comprises an interferogram, and wherein determining based, at least in part, on the light sensed by the image sensor, a first pressure measured at the first sensor and a second pressure measured at the second sensor comprises determining the first pressure and the second pressure based on a corresponding interferogram.

* * * * *